(12) United States Patent
Linares et al.

(10) Patent No.: US 8,979,937 B2
(45) Date of Patent: Mar. 17, 2015

(54) IMPLANTABLE ANKLE JOINT ASSEMBLY WITH SPHERICAL INTER-SUPPORT

(71) Applicants: Miguel A. Linares, Bloomfield Hills, MI (US); Linares Medical Devices, LLC, Auburn Hills, MA (US)

(72) Inventors: Miguel A. Linares, Bloomfield Hills, MI (US); Miguel A. Linares, Jr., Bloomfield Hills, MI (US)

(73) Assignee: Linares Medical Devices, LLC, Auburn Hills, MI (US)

( * ) Notice: Subject to any disclaimer, the term of this patent is extended or adjusted under 35 U.S.C. 154(b) by 292 days.

(21) Appl. No.: 13/628,693

(22) Filed: Sep. 27, 2012

(65) Prior Publication Data

US 2013/0090739 A1    Apr. 11, 2013

Related U.S. Application Data

(60) Provisional application No. 61/539,603, filed on Sep. 27, 2011.

(51) Int. Cl.
*A61F 2/42* (2006.01)
*A61F 2/30* (2006.01)

(52) U.S. Cl.
CPC ....... *A61F 2/4202* (2013.01); *A61F 2002/4205* (2013.01); *A61F 2002/4207* (2013.01); *A61F 2002/30014* (2013.01); *A61F 2002/30224* (2013.01); *A61F 2002/30253* (2013.01); *A61F 2002/30563* (2013.01); *A61F 2002/3064* (2013.01); *A61F 2002/30642* (2013.01); *A61F 2002/30878* (2013.01); *A61F 2002/30971* (2013.01)
USPC .................................... 623/21.18; 623/23.39

(58) Field of Classification Search
CPC ........... A61F 2/4202; A61F 2002/4205; A61F 2002/4207
USPC .......... 623/18.11, 19.11, 19.12, 20.22, 20.23, 623/21.11, 21.12, 21.13, 21.14, 21.15, 623/21.16, 21.17, 21.18, 21.19, 22.13, 623/22.16, 23.39, 23.4, 23.41
See application file for complete search history.

(56) References Cited

U.S. PATENT DOCUMENTS

| | | | |
|---|---|---|---|
| 5,092,898 A * | 3/1992 | Bekki et al. ................. | 623/22.16 |
| 6,436,146 B1 * | 8/2002 | Hassler et al. ............. | 623/21.11 |
| 6,926,739 B1 | 8/2005 | O'Connor et al. | |
| 7,534,246 B2 | 5/2009 | Reiley et al. | |
| 7,993,346 B2 | 8/2011 | Tornier et al. | |
| 8,187,308 B2 | 5/2012 | Mullaney et al. | |
| 2009/0287309 A1 * | 11/2009 | Walch et al. ............... | 623/18.11 |

* cited by examiner

*Primary Examiner* — David Isabella
*Assistant Examiner* — Suba Ganesan
(74) *Attorney, Agent, or Firm* — Gifford, Krass, Sprinkle, Anderson & Citkowski, P.C.; Douglas J. McEvoy

(57) ABSTRACT

A multi-component ankle joint assembly incorporated into reconditioned end surfaces established between an upper tibia bone and an opposing and lower talus bone. A first component is anchored into the upper tibia reconditioned end surface and exhibits a first exposed support surface. A second component is anchored into the lower talus reconditioned end surface of and exhibits a second exposed support surface. A spherical shaped intermediate component is supported in at least one of eccentric or rotational fashion between the first and second anchored components. The spherical shaped component includes a multi-layer composition having a softer outer layer and at least one harder interior layer establishing an eccentric rotational interface therebetween.

7 Claims, 5 Drawing Sheets

IMPLANTABLE ANKLE JOINT ASSEMBLY WITH SPHERICAL INTER-SUPPORT

CROSS REFERENCE TO RELATED APPLICATIONS

The application claims the priority of U.S. Ser. No. 61/539,603 filed Sep. 27, 2011.

FIELD OF THE INVENTION

The present invention discloses an artificial joint assembly, such as is particularly configured for employing as a retrofit ankle joint, and which combines multiple artificial components incorporated into first and second reconditioned joint defining surfaces for providing increased wear life in tandem with evenly distributed wear pattern/profile as well as enhanced flexibility and mobility.

BACKGROUND OF THE RELEVANT ART

An example of a prosthesis device for replacing articular surfaces of an ankle is depicted in U.S. Pat. No. 6,926,739, to O'Connor. Additional references depict an ankle replacement systems, such as shown in U.S. Pat. No. 7,534,246 to Reiley, as well as a method for implanting a malleolar implant in ankle joint such as is further shown in Tornier, U.S. Pat. No. 7,993,346. An example of an internal joint distraction device for providing articulation to an articulating bone joint between an upper bone structure and a lower bone structure is depicted in U.S. Pat. No. 8,187,308, to Mullaney.

SUMMARY OF THE PRESENT INVENTION

The present invention discloses a multi-component ankle joint assembly incorporated into reconditioned end surfaces established between an upper tibia bone and an opposing and lower talus bone. The assembly includes a first component anchored into the upper tibia reconditioned end surface and which exhibits a first exposed support surface. A second component is anchored into the lower talus reconditioned end surface of and exhibits a second exposed support surface. An intermediate component is supported in at least one of eccentric or rotational fashion between the first and second anchored components.

The intermediate component further exhibits a spherical shape, with each of the anchored components further exhibiting a concave surface for supporting the spherical shaped intermediate component. Each of the first, second and intermediate components may further be constructed of at least one of a metal, plastic, polymer or composite material.

The spherical shaped component further comprising a multi-layer composition including a softer outer layer and at least one harder interior layer. In a further application, the first and second inner layers establish an eccentric rotational interface therebetween.

A plurality of surface projecting bearings are mounted within an innermost spherical shaped portion of the spherical component and facilitate the eccentric rotational interface. An additional variant of the spherical supported bearing surfaces exhibits a grid pattern of lubricating grooves defined, such as is defined in a surface of an innermost spherical shaped portion of the spherical component for facilitating the eccentric rotational interface.

BRIEF DESCRIPTION OF THE DRAWINGS

Reference will now be made to the attached drawings, when read in combination with the following detailed description, wherein like reference numerals refer to like parts throughout the several views, and in which.

DETAILED DESCRIPTION OF THE PREFERRED EMBODIMENTS

As will be disclosed with succeeding reference to the several depicted embodiments, the present invention discloses an artificial joint assembly, such as is particularly configured for employing as a retrofit ankle joint, and which combines multiple artificial components incorporated into first and second reconditioned joint defining surfaces for providing increased wear life in tandem with evenly distributed wear pattern/profile as well as enhanced flexibility and mobility.

The joint assemblies described herein are particularly configured for such as in situ reconditioned installation within a patient's ankle joint (existing between lower facing end of the lower leg defined by tibia and proximately located fibula bones) and corresponding upper ends of the lower talus bone which defines an uppermost connecting location of a number of interconnected bones collectively defining the foot). It is further understood that certain applications could in theory include other joint applications, either human or other mammalian.

Also, and for purposes of ease and clarify of illustration, the various embodiments depicted further do not include reference to additional necessary components of the ankle joint, such as including associated muscles, tendons and ligaments, the inclusion of which are assumed and which collectively define a functioning and articulating ankle. These further include, without limitation, such as the anterior inferior tibiofibular ligament, the anterior talofibular ligament, the posterior inferior tibiofibular ligament, the posterior talofibular ligament and the calcaneofibular ligament, these extending at locations between the upper fibula or tibia and lower talus bone (upper part of foot defining a lower part of the ankle joint) or proximate calcaneus (heel) bone. A further rear positioned Achilles tendon (also not shown) is spaced from the ankle joint and extends from a posterior lower leg muscle to a rear upper location of the calcaneus (heel) bone.

Figure 1:
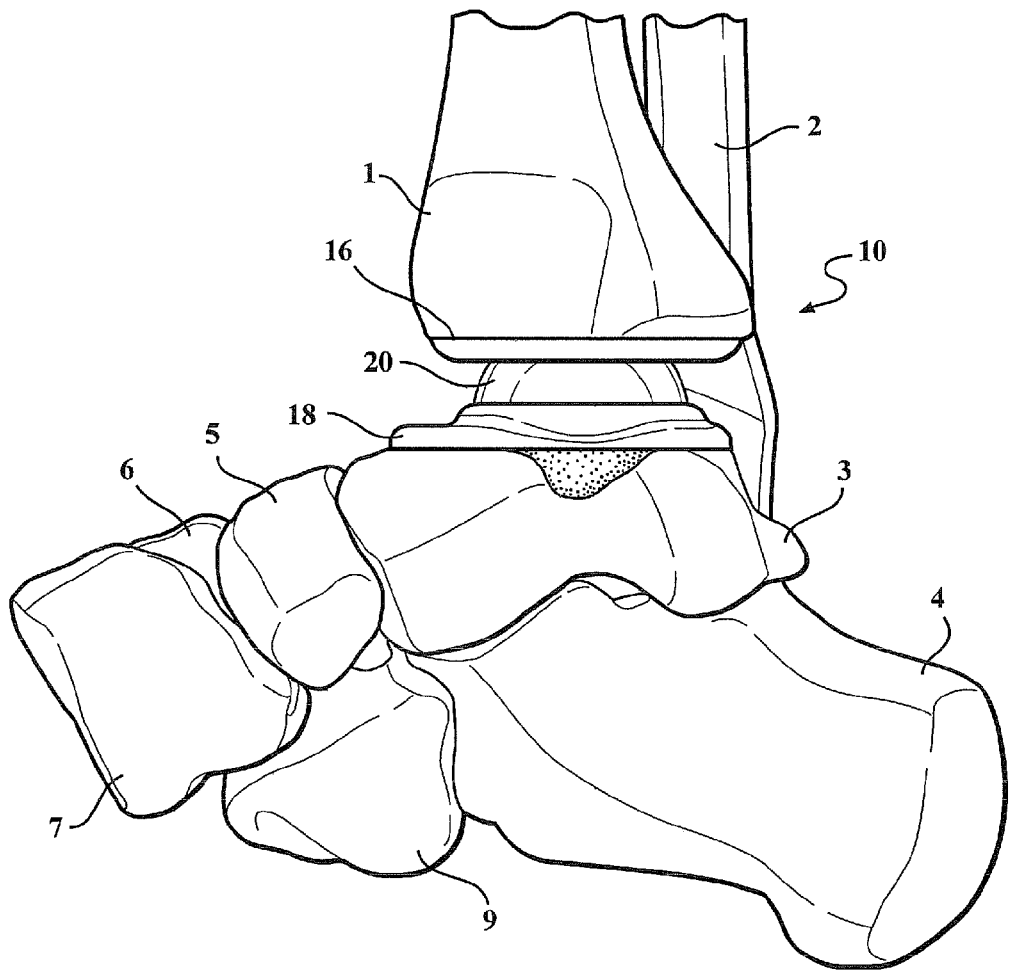
FIG. 1 is a perspective view of an ankle implant assembly according to the invention.
Figure 2:
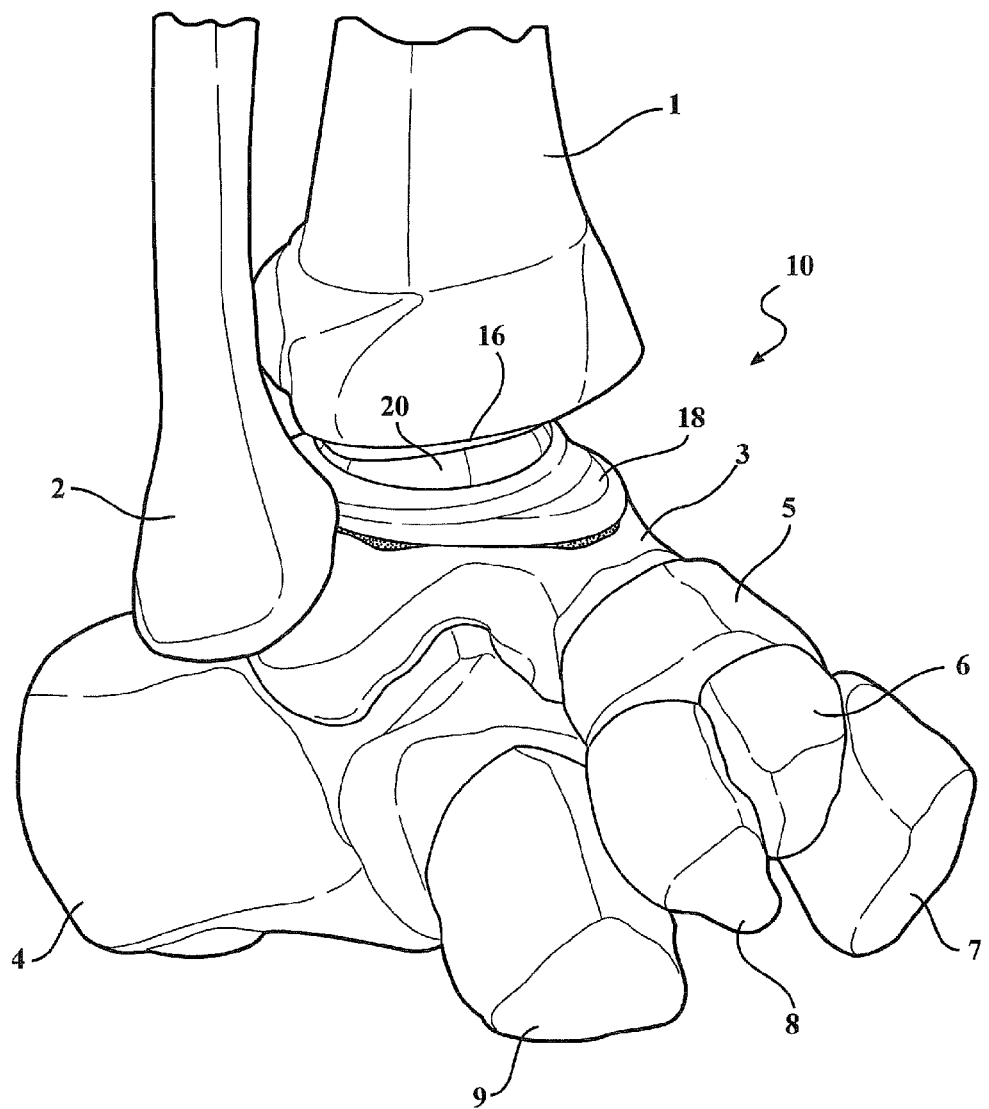
FIG. 2 is a rotated and slightly elevated perspective view of the assembly in FIG. 1 and again depicting the spherical inter support arranged between tibia and lower talus bone end secured implants.

Referring now to FIG. 1, a perspective view is generally shown at 10 of an ankle implant assembly according to an embodiment the invention and which is incorporated between an upper positioned tibia 1 and fibula 2 bones and a collection of lower opposing bones collectively defining the patient's foot and again including an uppermost and ankle joint defining talus 3 and proximate heel (or calcaneus) 4. An additional however incomplete recitation of additional foot bones depicted in each of FIGS. 1-3. These includes each of the navicular bone 5 (identified as a small tarsal bone found forwardly of tarsus 4) and the medial bone 6 (also known as the medial cuneiform or first cuneiform and is the largest of the cuneiforms situated at the medial side of the foot, anterior to the navicular and posterior to the base of the first metatarsal for articulating with four bone including each of the navicular, second cuneiform and first and second metatarsals). Additional bones identified include the transverse bone 7 (also termed transverse tarsal or midtarsal joint formed by the articulation of the calcaneus 4 with the cuboid 9 and the articulation of the talus 3 with the navicular 5, the lateral bone 8 (also termed lateral malleolus which defines the bony prominence on each side of the ankle) and, finally, the cuboid bone 9 which is the lower and lateral most positioned of the seven foot tarsal bones.

Figure 3:
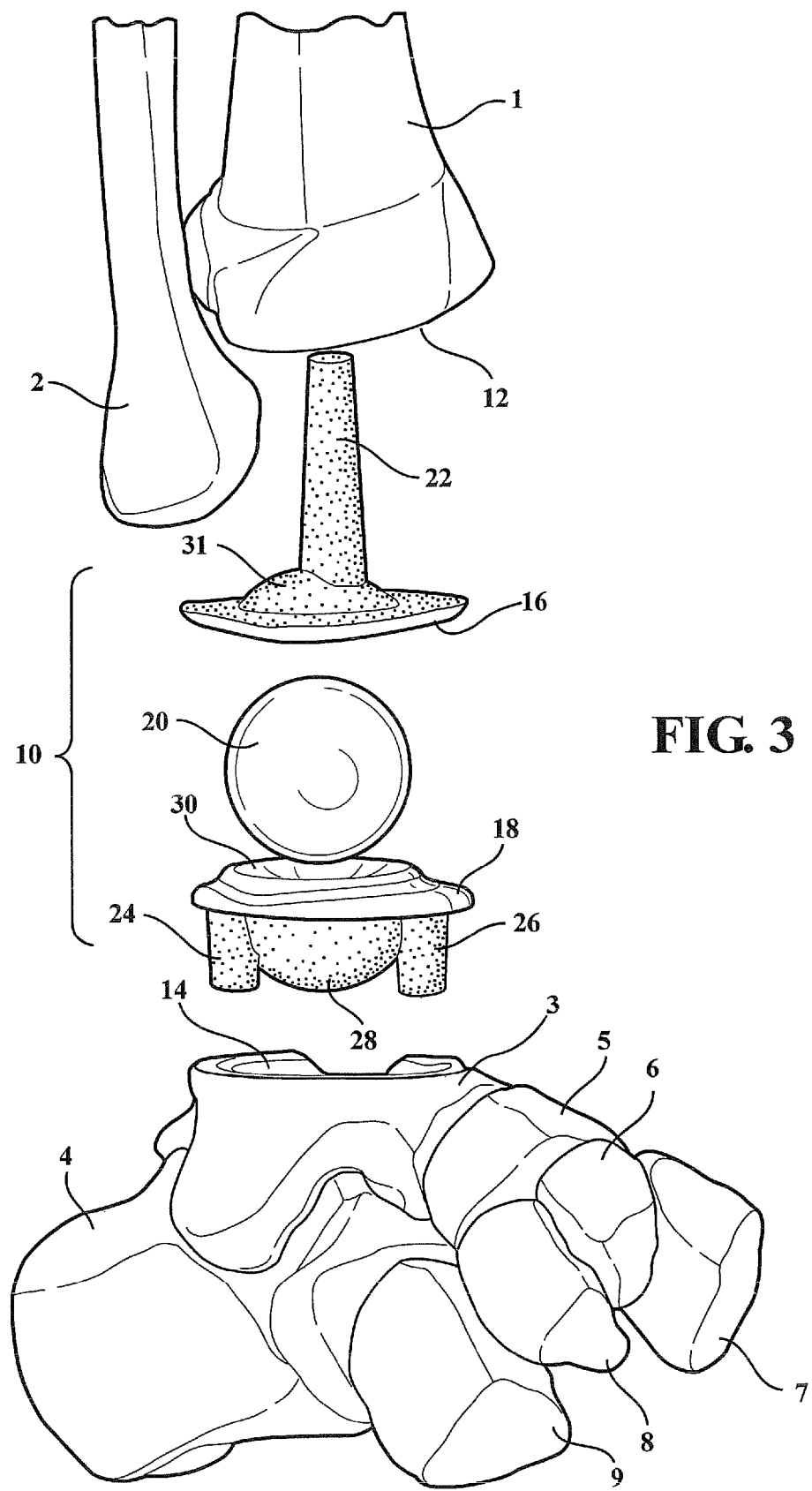
FIG. 3 is an exploded view of the ankle implant assembly in substantially the position of FIG. 2 and better illustrating the reconditioned end-configurations established between the tibia and talus bones, combined with end face seating and marrow growth promoting implant support inserts in combination with intermediate positioned and eccentrically supported spherical portion.

Having described in some detail the bone construction of the lower leg and foot defining the ankle proximate joint, reference is further best made in exploded FIG. 3 to in situ reconditioning of the bone ends, illustrated by conditioned end profile 12 configured into the bottom most end surface of the tibia 1, as well as opposing upper end facing and recessed/reconditioned profile 14 defined in the upper most opposing end of the talus 3. According to one non-limiting surgical procedure, such in situ reconditioning can occur following incision or removal of any remaining damaged bone and/or cartilage associated with the damaged joint and during an appropriate surgical procedure utilizing medical drilling, boring and shaping instruments in order to recondition the joint defining bone ends and to create the desired shaping and profile of the joint. As previously indicated, it is advantageous to refashion the joint end profiles in situ during an appropriate surgical procedure, a further objective being to retain or repair, where possible, natural ligament, cartilage and muscle associated with a normal functioning joint.

Although not shown, such reconditioning can be employed with minimal interference to such necessary additional elements of the ankle joint including associated ligaments, muscles and tendons. Without limitation, it is further understood that the joint assemblies described in each of the illustrated variants can be integrated into either of human or synthetic bones (such as which can also contemplate both human and synthetic bones in a single joint application), with such joint assemblies also capable of surgically implanted in either total or partial fashion concurrent with any necessary degree of refashioning or removal of damaged bone or joint.

A set of bone end installable implant portions are depicted at 16 and 18 with each exhibiting a rear facing profile suitable for anchoring into the respective reconditioned end face configurations 12 and 14 defined in the tibia 1 and talus 3, respectively. The fibula bone 2 is further shown in a generally original arrangement with the further understanding that a suitable reconditioning of its associated end with the lateral offset position of the talus can also be reconditioned to some degree as is necessary.

Each of the implant portions 16 and 18 are constructed of any arrangement of metal, polymer, plastic, composite or other suitable material, with it further being understood that the individual pairs of components can be arrayed with any pattern of alternating materials, such that the components 16 and 18 being constructed of a first material, with an intermediate and inter-positioned spherical shaped bearing or ball portion 20 positioned therebetween and being constructed of a second alternating material. Although depicted as a spherical shaped element, the present invention contemplates the ankle joint including any potentially reconfigurable opposing recessed profiles associated with implant portions 16 and 18, and which may further be provided in combination with an alternately (i.e. non-spherical) shaped intermediate component including any type of cylindrical, pseudo cylindrical, oblong, oval ellipsoidal or other smooth shape. In this fashion, the desired wear properties and profiles are adjusted in part based upon the material selection of the individual components with concurrent objectives being both equalization of overall wear patterns established between the respective pairs of components and determining those situations in which metal on metal or plastic on plastic contact between the components is either desired or, more often, not.

A suitable medical adhesive, cement or other fastener can be employed for securing each of the upper component 16 and lower component 18 into the respective reconditioned joint defining end surfaces 12 and 14 of the tibia 1 and talus 3. As further best shown in FIG. 3, each of the reconditioned bone ends includes an interior extending aperture (not shown) which is formed by a suitable bone drill and within which are seated rearward extending anchoring stems including that depicted at 22 associated with a rear mounting profile of the upper insert 16 into the lower end of the tibia 1, as well as the combination of lower stems 24 and 26 and intermediate rear profile dome 28 for mounting the lower insert 18 into the upper end of the tarsus 3.

Each of the end face mounted implants 16 and 18 further exhibits a concave exterior facing profile and which includes a more pronounced and substantially hemi-spherical cavity 30 (FIG. 3) associated with the reconditioned interior of the talus 3, with an opposing and lesser pronounced/shallower concave seating cavity (not shown but best evident from FIG. 1) being associated with the underside of the upper insert 16. Upon securing the implants 16 and 18 within the reconditioned end face locations 12 and 14 of the bones 1 and 3, these collectively define upper and lower seating locations for supporting the interposed spherical element 20 as best depicted in rotated perspectives of FIGS. 1 and 2 in a designed range of eccentric articulating ranges as permitted by the joint construction.

As further previously noted, the concave shaped recess profiles can each be constructed of a smooth lubricant entrained or other polished plastic, composite or metal surface, with the exterior configuration of the spherical support 20 again being constructed of an alternating material, such as to reduce and equalize wear profiles, as well as to enhance operational range and effectiveness.

As again previously indicated, additional configurations of muscles, ligaments, tendons are provided and can include both natural and/or synthetic materials which can be implanted or reconstructed in order to provide a dynamic and long-term implantable assembly. As shown in FIG. 3, the seating or inserting rear faces of the upper mounted implant portions 16 (including rear base surface 31 side of upper implant 16 converging to inwardly extending stem 22) and further opposing implant portion 18 (including each of posts 24 and 26 and intermediate dome 28) can each further include an undercut textured or otherwise roughened consistency, this contributing to promotion of bone marrow in-growth into the implant portions following such as initial adhesive and seating affixation, such bone growth contributing to long term retention of the implant.

Figure 4:
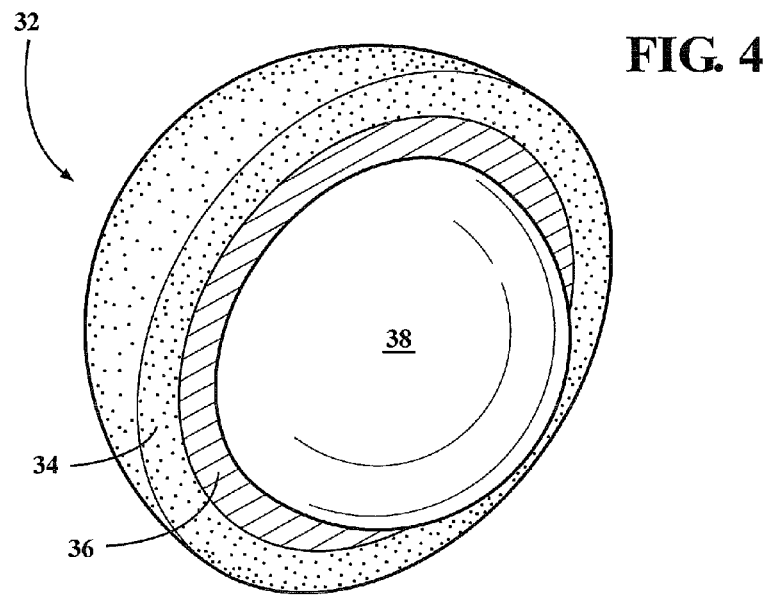
FIG. 4 is a pseudo cutaway view of a spherical shaped intermediate support and which illustrates its multi-material construction with softer outermost shell material and intermediate harder material in cutaway, combined with innermost harder core material in spherical perspective and which further evidences an eccentric rotatable interface established between said intermediate and innermost layers.

Referring now to FIG. 4, a cutaway view is generally shown at 32 of a selected spherical inter-movable support, such as again represented by the spherical ball disclosed in the preceding described variant of FIG. 1. The pseudo cutaway view of FIG. 4 illustrates one non-limiting example of a multi-layer material construction and which includes a softer (typically plastic or plastic composite) outermost material layer 34, an intermediate harder 36 material (typically another plastic), and an innermost harder material 38 (which is depicted in un-sectioned spherical perspective shape and can be of a similar hardness as the intermediate layer 36 as well as potentially including either of a relatively harder or softer material based on the specifics and preferences of the application).

In operation, an eccentric rotatable interface is established between the intermediate 36 and innermost (or core) 38 layers, this typically arising from the compressive aspects exerted on the softest outer shell layer 34 by both the upper and lower associated implants resulting in a degree of inter-rotative offset or eccentric give or play established at the interior interface boundary between the intermediate layer 36 and the inner core 38. The outer compressive exerted forces typically result from any inwardly angular directed force exerted on the intermediate spherical element, and such as is defined as a non-tangential force.

Figure 5:
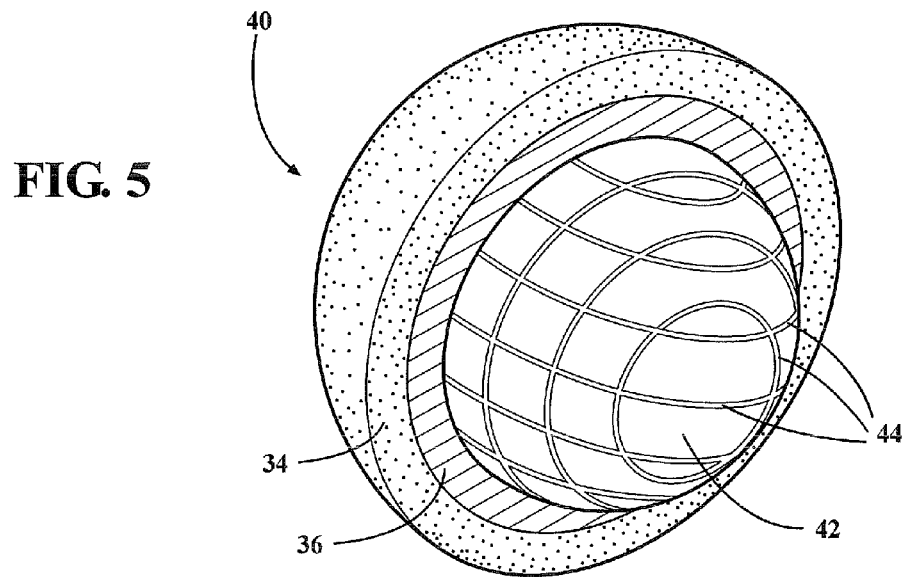
FIG. 5 is a pseudo cutaway view of a spherical shaped intermediate support similar to that in FIG. 4 and further depicting a plurality of lubricant supporting grooves defined in a surface grid pattern associated with the innermost hardened core.

FIG. 5 is a similar pseudo cutaway view, generally at 40, of a spherical shaped intermediate support similar to that in FIG. 4, with identical outer soft shell 34 and intermediate harder shell 36, and in which an innermost core is reconfigured as shown at 42 with a grooved arrangement 44. The grooves 44 can facilitate eccentric motion in the interior boundary defined between layers 36 and 42, in the manner previously described, and/or can also includes entrainment of a volume of lubricant supported within the grooves 44 in a fairly evenly distributed fashion associated with the hardened core 42.

It is also envisioned and understood that the spherical ball, grooves or other supporting structure can include small entrapment channels or pockets for retaining micro particles of debris, either or both plasticized resulting from wear of the implant portions and bone, and such as is further defined as debris osteolysis. The ability to segregate and remove such micro particles (again using the pattern of grooves 44 or other suitable arrangement) assists in extending useful life of the implant along with reducing pain, squeak/noise or other undesirable aspects typical of previous implant designs.

Figure 6:
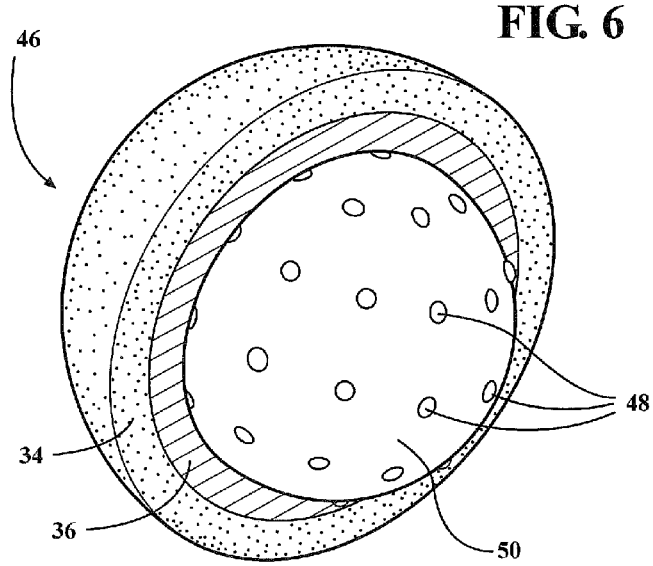
FIG. 6 is a further cutaway view which is again similar to FIG. 4 and further depicting a plurality of substantially surface embedded ball bearings associated with the inner most core.
Figure 7:
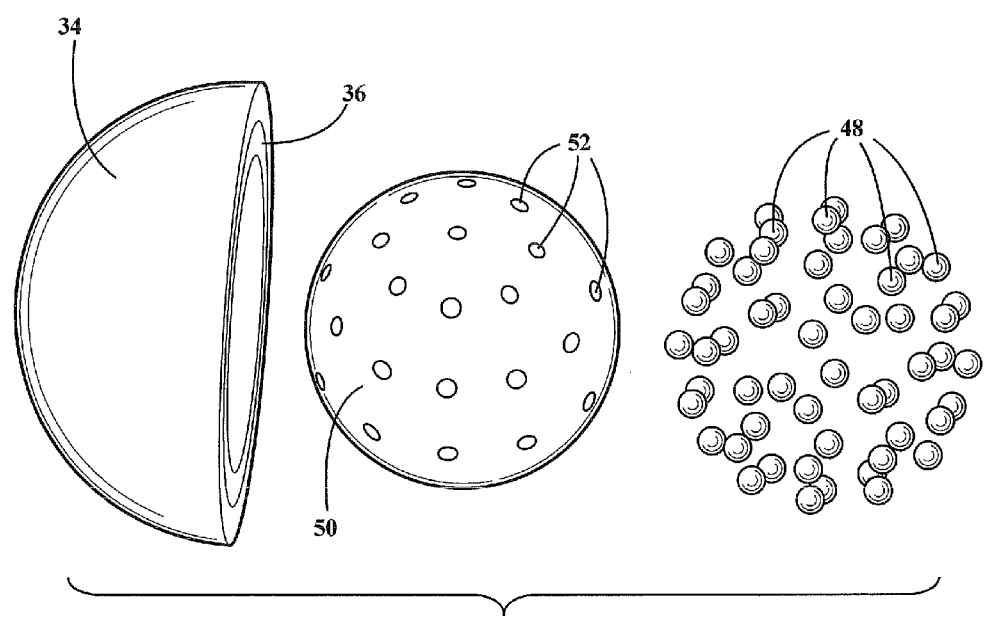
FIG. 7 is an exploded view of the cutaway of FIG. 6 and which better illustrates the arrangement of micro sized ball bearings in combination with the seating locations arranged about the spherical exterior surface of the harder core material.

Referring now to FIG. 6, a further cutaway view is generally shown at 46 which is again similar to FIG. 4 and further depicting a plurality of substantially surface embedded ball bearings 48 (such as which can be constructed of metal, plastic, plastic composite or other suitable material) associated with a further redesigned version of an inner most core 50. As best depicted in the further exploded view of FIG. 7, the ball bearings 48 are separated from the hardened inner spherical core 50, thereby revealing substantially spherical shaped pockets 52 defined across the exterior profile of the core 50 and which substantially seat the individual bearings 48 in a manner which permits the tips thereof (again FIG. 6) to project in a manner which facilitates additional eccentric support motion with respect to the interior interface boundary established with the intermediate later 36 in a manner consistent with the dynamic environments referenced in relation to FIGS. 4 and 6.

Having described my invention, other and additional preferred embodiments will become apparent to those skilled in the art to which it pertains, and without deviating from the scope of the appended claims.

We claim:

1. A multi-component ankle joint assembly incorporated into reconditioned end surfaces established between an upper tibia bone and opposing lower talus bone, said assembly comprising:
a first implant adapted to being anchored into the upper tibia reconditioned end surface and exhibiting a first exposed support surface;
a second implant adapted to being anchored into the lower talus reconditioned end surface of and exhibiting a second exposed support surface;
an intermediate component supported in at least one of eccentric or rotational fashion between said first and second anchored implants;
each of said implants further exhibiting concave inner facing surfaces for supporting said intermediate component therebetween;
said first implant further having a convex rear surface, a stem extending from said convex rear surface which is adapted to seat within the reconditioned tibia; and
said second implant further having a dome shaped rear surface separating a pair of lower stems adapted to seat within the reconditioned talus.

2. The joint assembly as described in claim 1, said intermediate component further comprising a spherical shaped component.

3. The joint assembly as described in claim 2, said spherical shaped component further comprising a multi layer composition including at least one outer layer surrounding an innermost spherical shaped portion.

4. The joint assembly as described in claim 3, said at least one outer layer further comprising a softest outer most layer and an intermediate harder layer and establishing an eccentric rotational interface therebetween.

5. The joint assembly as described in claim 4, further comprising a plurality of surface projecting bearings partially seating within substantially spherical shaped pockets configured within said innermost spherical shaped portion and which are communicable with said intermediate layer for facilitating said eccentric rotational interface.

6. The joint assembly as described in claim 4, further comprising a grid pattern of lubricating grooves defined in a surface of said innermost spherical shaped portion facilitating said eccentric rotational interface.

7. The joint assembly as described in claim 1, each of said first and second implants and said intermediate component further being constructed of at least one of a metal, plastic, polymer or composite material.

* * * * *